(12) United States Patent
Rose (10) Patent No.: US 7,023,364 B2
(45) Date of Patent: Apr. 4, 2006

(54) MEDICAL KEYBOARD

(75) Inventor: Gregory Hugh Rose, Bellaire, TX (US)

(73) Assignee: Rocoview, Inc., Bellaire, TX (US)

( * ) Notice: Subject to any disclaimer, the term of this patent is extended or adjusted under 35 U.S.C. 154(b) by 401 days.

(21) Appl. No.: 10/662,921

(22) Filed: Sep. 15, 2003

(65) Prior Publication Data
US 2004/0061630 A1   Apr. 1, 2004

Related U.S. Application Data (60) Provisional application No. 60/411,047, filed on Sep. 16, 2002.

(51) Int. Cl.
*H03M 11/00* (2006.01)

(52) U.S. Cl. .................. 341/20; 400/486; 400/487; 715/710

(58) Field of Classification Search ............ 341/20, 341/22; 400/486, 487; 345/168, 170; 715/700
See application file for complete search history.

(56) References Cited

U.S. PATENT DOCUMENTS

| | | | |
|---|---|---|---|
| 4,101,883 A | | 7/1978 | Hempenius et al. |
| 5,297,041 A | * | 3/1994 | Kushler et al. .............. 715/534 |
| 5,600,313 A | * | 2/1997 | Freedman ..................... 341/22 |
| 5,818,361 A | * | 10/1998 | Acevedo ....................... 341/23 |
| 5,905,493 A | * | 5/1999 | Belzer et al. ................ 715/835 |
| 5,936,554 A | * | 8/1999 | Stanek ........................ 341/22 |
| 6,961,048 B1 | * | 11/2005 | Mitchell ..................... 345/168 |

* cited by examiner

*Primary Examiner*—Albert K. Wong
(74) *Attorney, Agent, or Firm*—Wong, Cabello, Lutsch, Rutherford & Brucculeri, LLP (57) ABSTRACT

A computer keyboard designed to facilitate and simplify a user's interaction with medical software applications includes color-coded key groups and function specific icons. One key group is associated with medical image display tasks such as, for example, the display of Computed Tomography (CT) scans, Magnetic Resonance Imaging (MRI) scans and ultrasound scans of various portions of a patient's body. Another key group is associated with medical image navigation tasks such as moving to the next, previous, first or last image in a group of images. Each key in each key group has a function-specific indicator that identifies the key's function for a specified medical software application. For example, a key group associated with medical image acquisition for a radiographic software application may include keys having icons and/or text representing predetermined body regions such as the head, neck, lung, liver, knee, abdomen, bone, spine, mediastium, pelvis and/or whole body.

23 Claims, 13 Drawing Sheets

LUNGS

ABDOMEN

LIVER

HEAD

KNEE

NECK

MEDIASTINUM

MRI $T_1$

MRI $T_2$

SCOUT

ULTRASOUND

MEDICAL KEYBOARD

RELATED APPLICATIONS

This application is related to U.S. patent application Ser. No. 60/411,047 (filed 16 Sep. 2002), to which priority is claimed under 35 U.S.C. 120 and which is incorporated herein by reference.

BACKGROUND

The invention relates generally to keyboards for computer systems and more particularly, but not by way of limitation, to keyboards for use in computer systems executing medical software application programs.

As computer processing capability and user-interface technology has improved, computer systems have been employed in ever more applications. In the medical field, for example, physicians now routinely use computers (e.g., workstations, personal computers and personal digital assistants) to display and analyze medical data.

Conventional image-based medical systems include an imaging device coupled to one or more workstations and one or more server computer systems through a computer network. In practice, the workstations execute medical software application programs that permit the user to display, navigate and manipulate medical images generated by the imaging device. Illustrative imaging devices include Computed Tomography (CT), Magnetic Resonance Imaging (MRI), ultrasound and X-ray scanners. During evaluation, acquired images are displayed on the workstation's display and manipulated via input devices such as, for example, a keyboard and/or a pointer device.

Typical medical software applications (e.g., radiographic and cardiology software applications) include large numbers of functions a physician may use to display, manipulate and evaluate acquired images. These functions typically provide for not only the adjustment and analysis of the images themselves, but also navigation through the images, sorting of images, grouping of images, access to associated patient information and various dictation functions.

Figure 1:
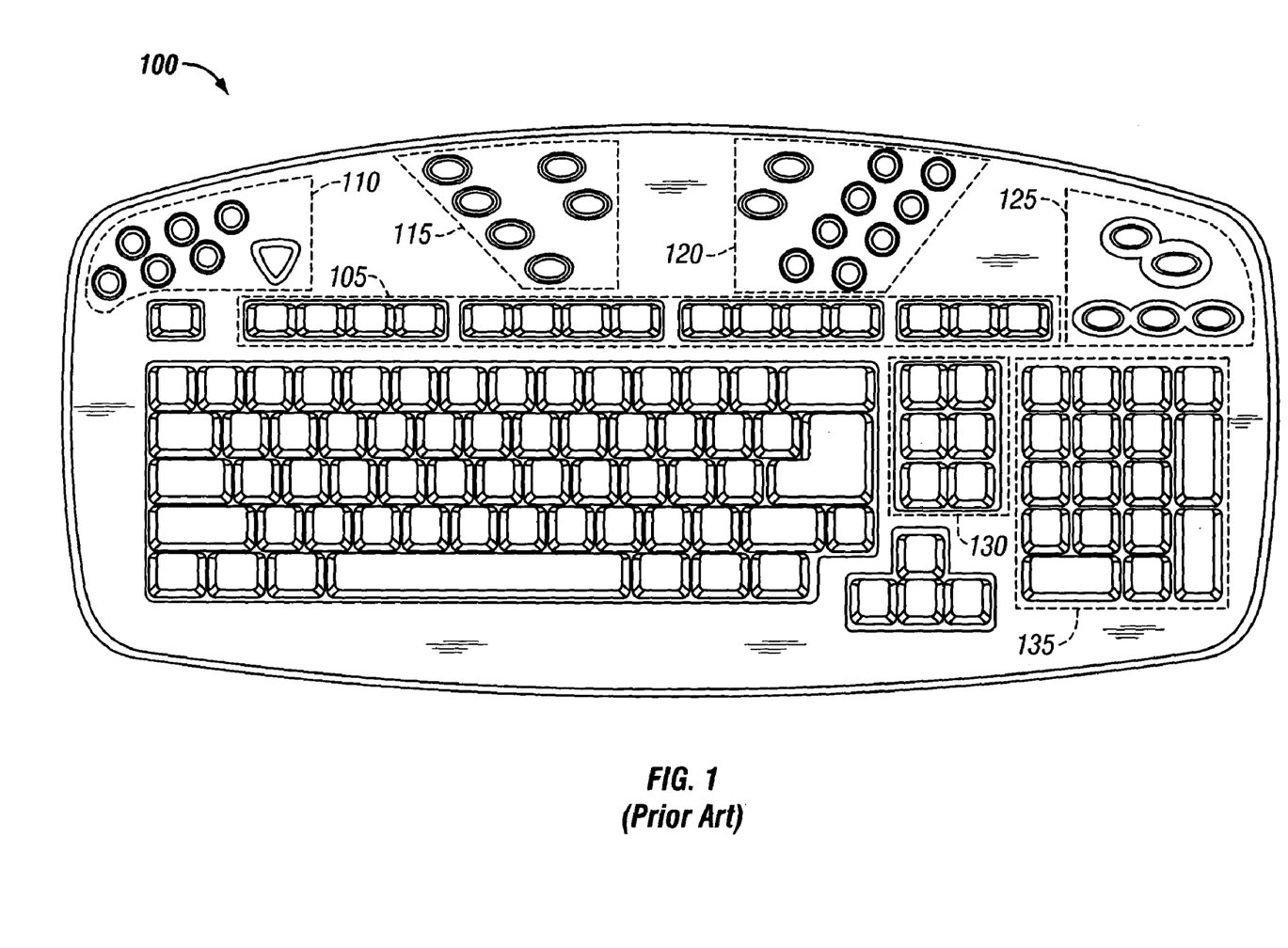
FIG. 1 shows a prior art keyboard.

Referring to FIG. 1, current medical software application programs use standard keyboards such as keyboard 100 for user input. Such keyboards force the user/interpreter to either memorize special functions associated with one or more keys, write down the functions associated with specified keys on strips of paper and place them adjacent to the keys, repeatedly reference a key-code sheet or "hunt-and-peck" until the correct function is performed. It is typical, for example, that function keys 105 (F1 through F15) as well as other key groups (e.g., key groups 110 through 135) are programmatically assigned functions by the medical software application (either by default or by user action). The large number of functions and keys make it difficult for a physician to effectively use the medical software application. Thus, it would be beneficial to provide a keyboard that simplifies a user's task of using medical software applications.

SUMMARY

The invention provides a keyboard for use with medical software application programs. Illustrative medical software application programs include those designed for use in the radiology, cardiology, orthopedic and dental fields. In one embodiment, a first visually distinct key group includes keys having icons representative of medical image display functions and a second visually distinct key group includes keys having indications of medical image navigation functions. In one embodiment, keys in the first key group have icons that depict predetermined body regions such that when activated, the displayed image is optimized for viewing that body region represented by the activated key's icon.

In another embodiment, a third visually distinct key group is provided that includes keys associated with medical image manipulation functions. In yet another embodiment, a fourth visually distinct key group is provided that includes keys associated with patient information retrieval, modification and creation functions.

DETAILED DESCRIPTION

Computer keyboards to facilitate and simplify a user's interaction with medical software applications are described. The following embodiments of the invention, described in the context of a radiographic imaging computer system and associated application programs, are illustrative only and are not to be considered limiting in any respect. For example, the claimed computer keyboard is equally applicable to other medical fields such as cardiology, ophthalmology and dentistry.

Figure 2:
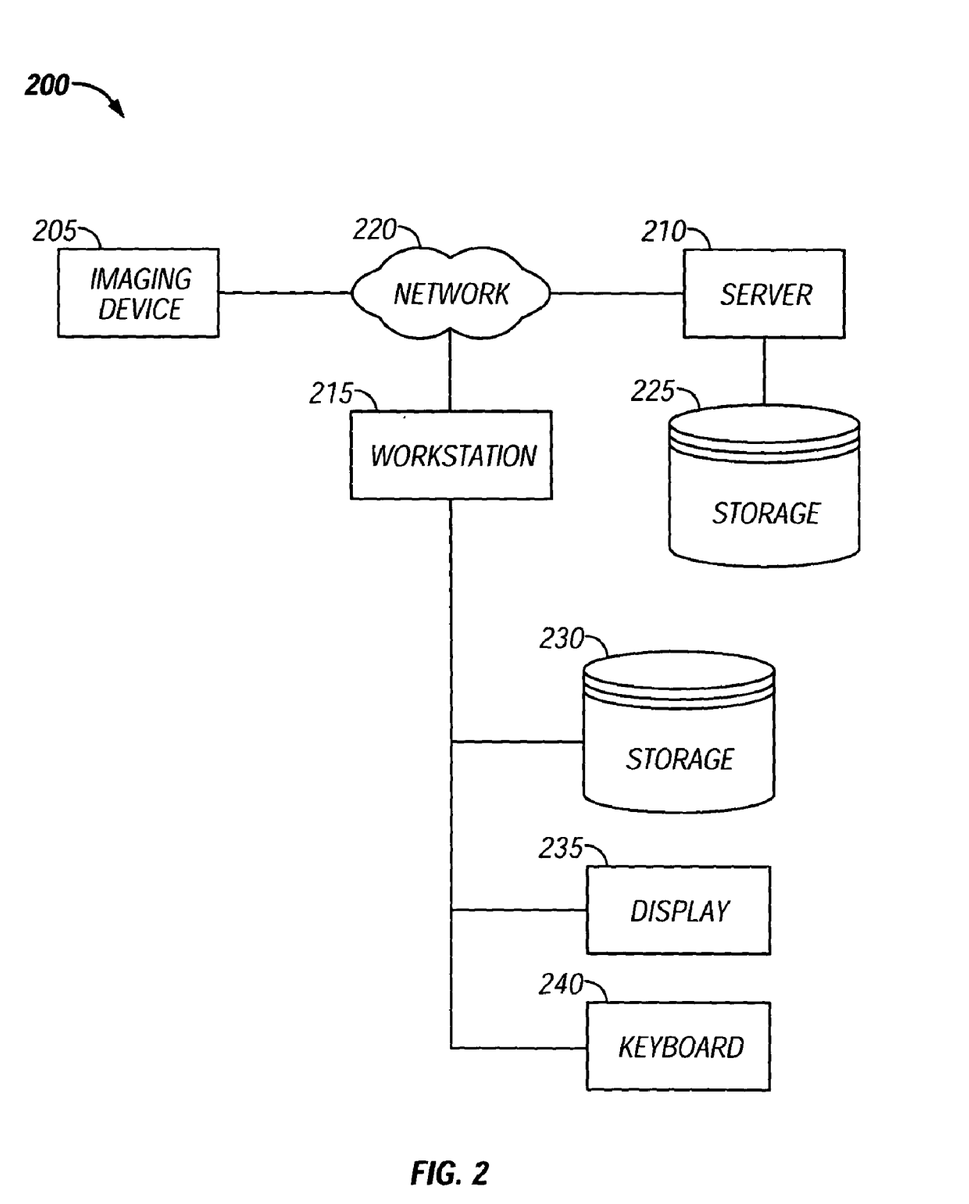
FIG. 2 shows, in block diagram format, an radiographic computer system in accordance with one embodiment of the invention.

Referring to FIG. 2, radiographic computer system 200 in accordance with one embodiment of the invention comprises imaging device 205, one or more server computer systems (only server 210 is shown) and one or more workstations (only workstation 215 is shown) coupled via computer network 220. As previously noted, illustrative imaging devices include CT, MRI, ultrasound and X-ray scanning devices. Server 210 may be used for network administrative functions and typically includes one or more long-term storage devices (e.g., storage 225) such as magnetic disks, magnetic tape units, optical disks and combinations thereof. Network 220 may be a direct communication link between imaging device 205, server 210 and workstation 215, a medical facilities intranet or may include the Internet. Workstation 215 is typically a personal computer and includes one or more storage devices (e.g., storage device 230), display 235, keyboard 240 and a pointer device such as a track-ball or mouse (not shown).

A significant aspect of radiographic computer system 200 is the interface through which the user (a radiologist) interacts with the medical software application program—i.e., that application program that executes on server 210 and/or workstation 215 which is used to control image retrieval, display and manipulation.

Modern medical application programs are complex and, in an attempt to ease a user's burden, map large numbers of functions to specified keys on keyboard 240. It has been found that assigning functions associated with a specific type of operation (image display, image navigation, image manipulation, patient information, etc.) to independently identified key groups and using uniform icons and unique display characteristics (e.g., color and/or key shape) within each key group to identify a key's specific function, greatly improves a physician's ability to perform their evaluation and document their medical analysis. This, in turn, can speed a physician's evaluation and reduce the number of documentation and/or reading errors associated with the evaluation.

Figure 3:
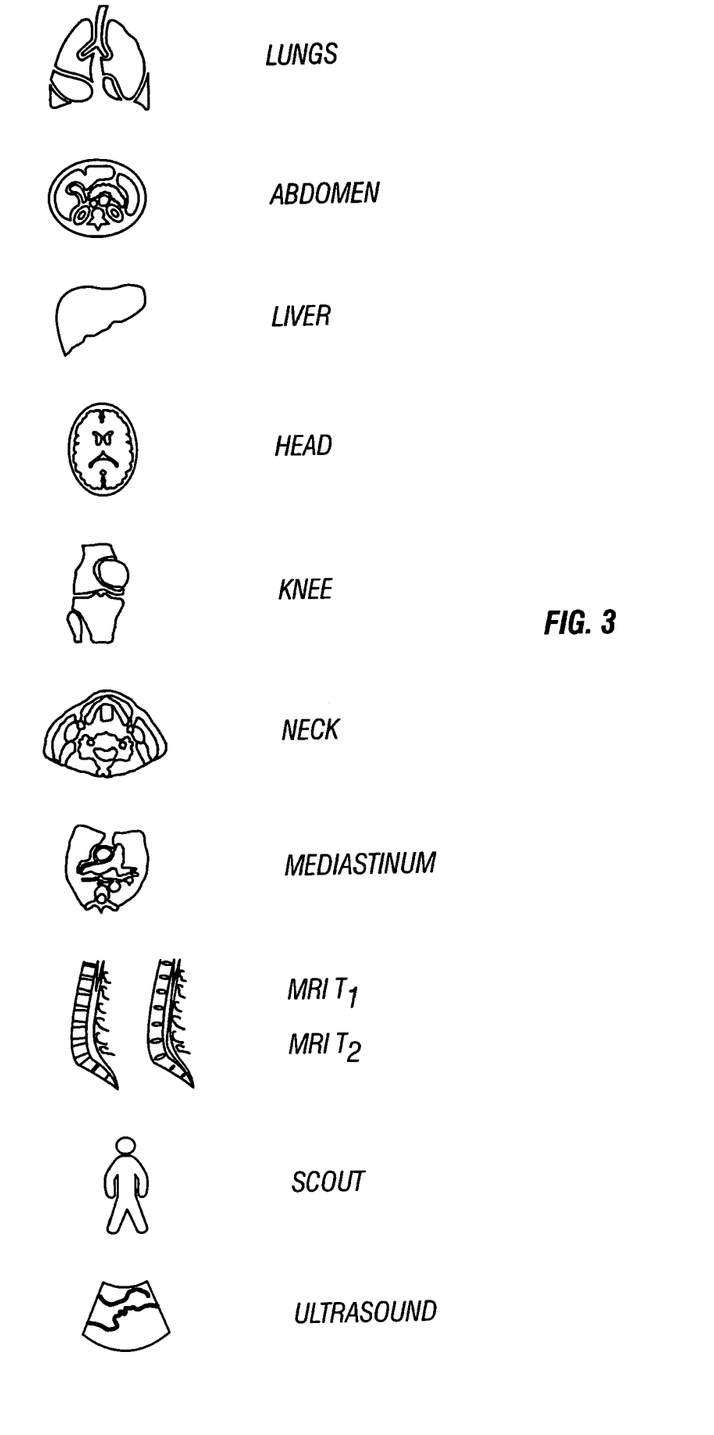
FIG. 3 shows icons used in one embodiment of the invention for invoking image display functions.

In one embodiment, a first key group is assigned functions associated with radiological image display. These keys, having a first color and/or shape to distinguish them from standard keyboard keys and/or other key groups, may include keys for displaying images of a patient's: (1) lungs; (2) abdomen; (3) liver; (4) head; (5) knee; (6) neck; (7) mediastinum; (8) spinal region—T1 and T2 views; (9) a scout image (a low resolution whole-body scan); or (10) an ultrasound image. Icons representing these anatomic regions (or other regions of choice) are affixed to or made part of each key in the first key group. Illustrative icons for each of the above-identified regions are shown in FIG. 3.

In practice, a physician displays one or more images in a series acquired during a patient study. If the image is of the neck region, the key having the "neck" icon is depressed causing the window and level presets to change to those values previously determined to be optimal when viewing the neck region. Similarly, if the image being viewed is of a patient's knee, the "knee key" is depressed causing the window and level presets to change to those values previously determined to be optimal when viewing the knee region. In general, each key is associated with display preset values (e.g., window and level values) appropriate to the body region identified on the key's icon (and/or text label).

A second key group may be assigned functions associated with image navigation functions. These keys may be identified by a second color and/or shape to distinguish them from standard keyboard keys and other key groups and may include keys for navigating through a plurality of acquired patient images. Illustrative image navigation functions include going to the: (1) first image in a group of images; (2) the next image in a group of images; (3) the previous image in a group of images; (4) the last image in a group of images; (5) the next series of images in a study; and (6) a prior series of images in a study. Keys in the image navigation key group may have icons and/or descriptive words to identify their function.

Figure 4:
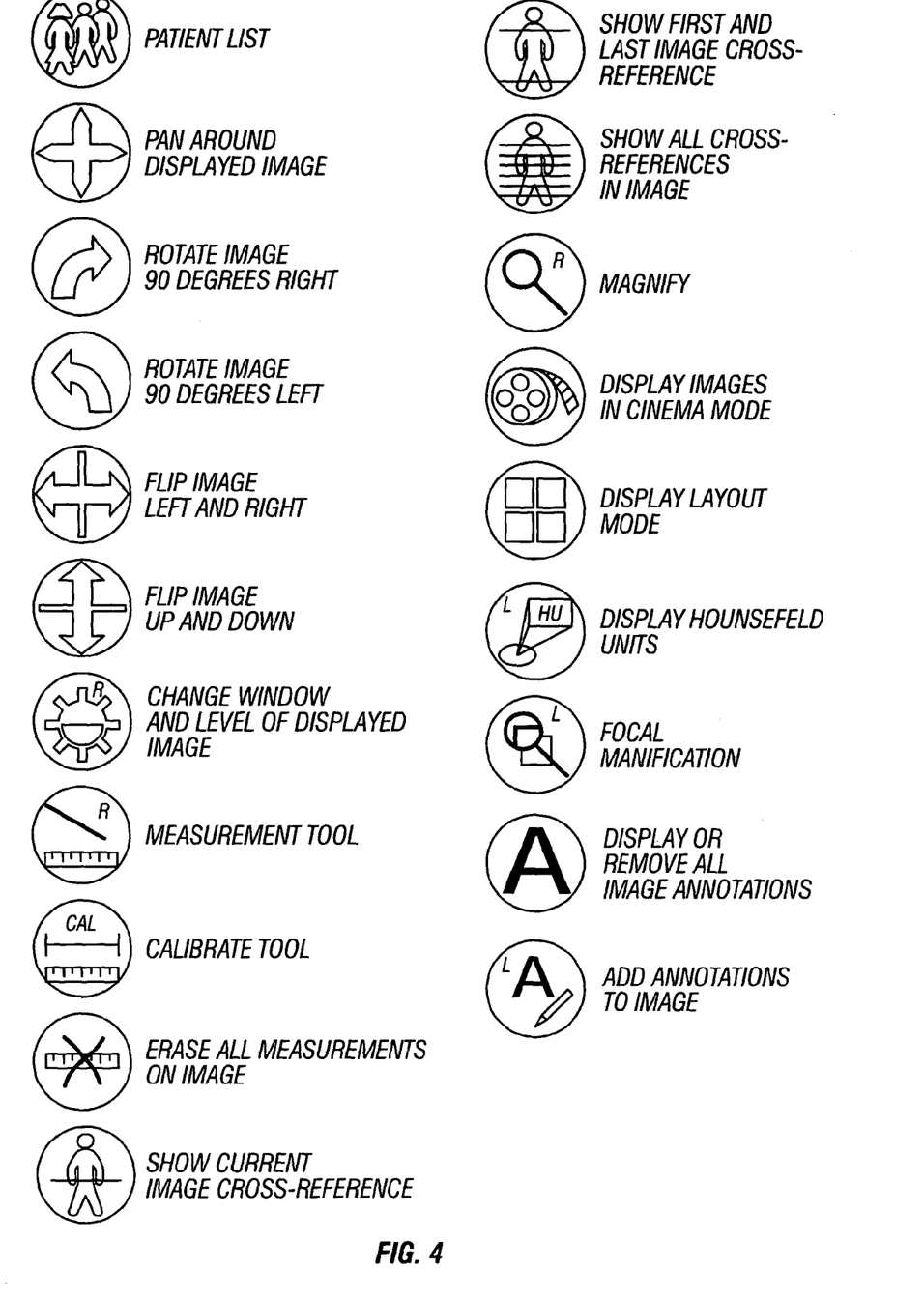
FIG. 4 shows illustrative icons for invoking image manipulation functions in accordance with one embodiment of the invention.

A third key group may be assigned functions associated with image manipulation. Keys in this group may be identified by a third color and/or shape to distinguish them from standard keyboard keys and other key groups. Functions typically associated with keys in this group include: (1) the activation of image measurement tools; (2) invocation of image correlation procedures; (3) patient listing operations; (4) identification of "regions of interest" in a displayed image and the presentation of detailed information regarding that region (e.g., tissue density); (5) adjusting the displayed image's level up; (6) adjusting the displayed image's level down; (7) adjusting the displayed image's window down; and (8) adjusting the displayed image's window down up. (One of ordinary skill in the art will recognize that the window and level adjustment functions alter display characteristics of the image by changing the image's display threshold as measured in Hounsfeld units.) It will be recognized by those of ordinary skill in the art that while the precise mechanisms to implement these functions and the range of functions provided are unique to the medical software application program used to display the images, many such application programs provide functionally similar operations. Illustrative icons for representing a set of image manipulation operations are shown in FIG. 4.

A fourth key group may be assigned functions associated with patient information retrieval and manipulation. Keys in this group may be identified by a fourth color and/or shape to distinguish them from standard keyboard keys and other key groups. Functions typically associated with keys in this group include: (1) retrieving a patient's medical history; (2) dictating a physicians report; (3) show other studies preformed; (4) show reports from prior studies; and (5) paperless fax report.

Figure 5:
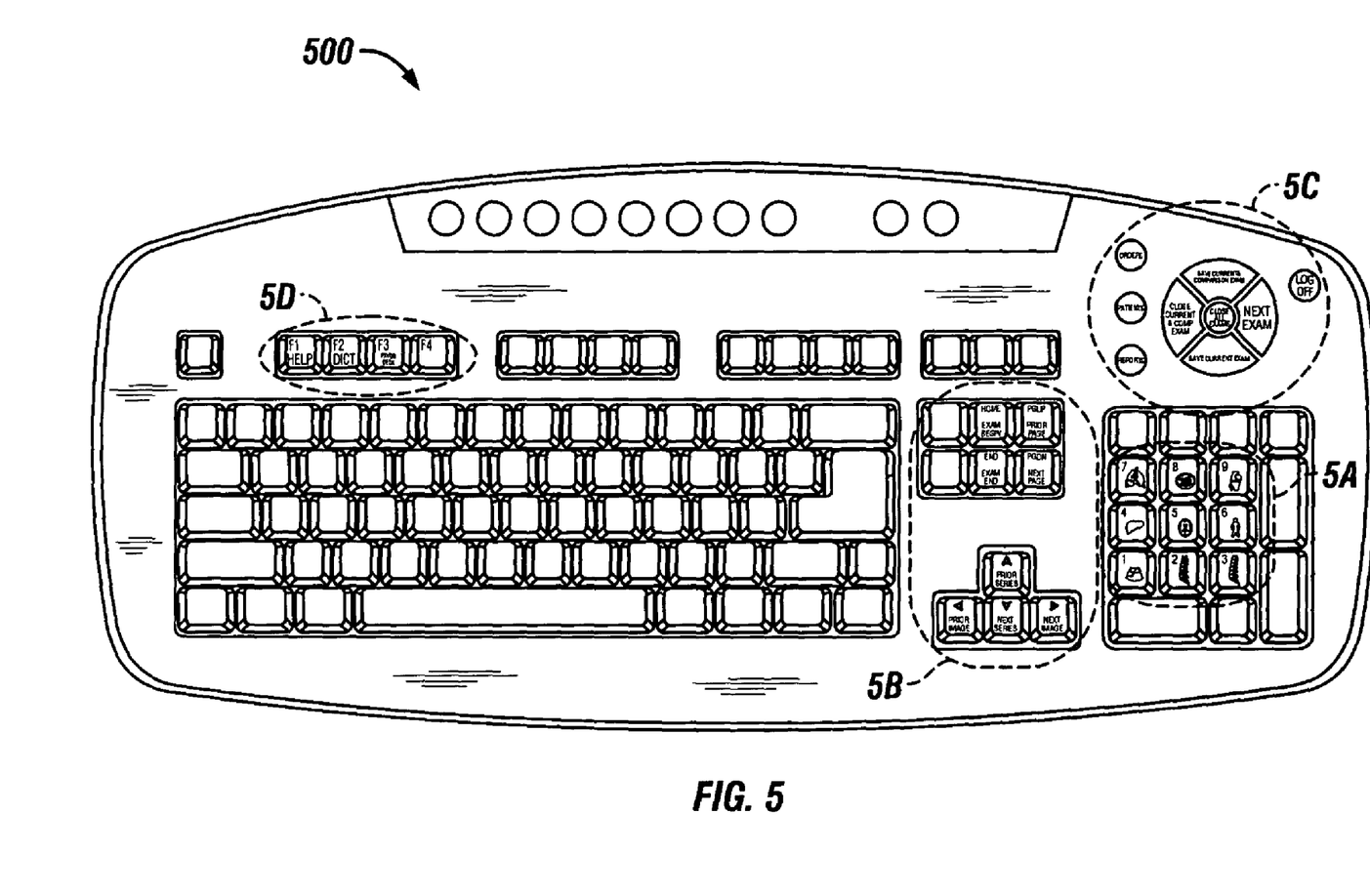
FIG. 5 shows a keyboard in accordance with one embodiment of the invention.
Figure 5A:
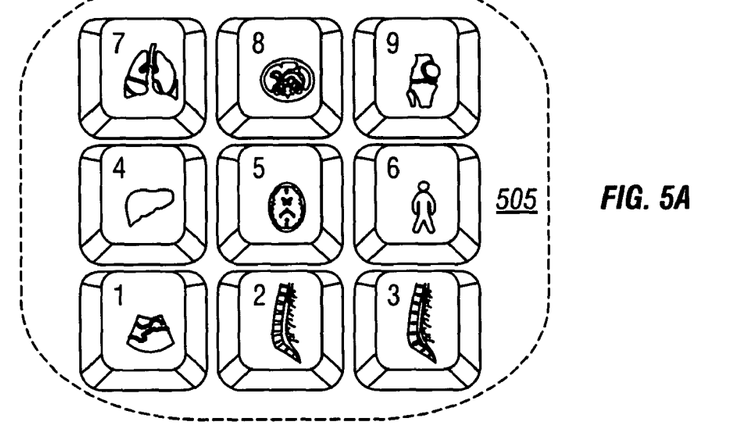
FIGS. 5A through 5D show expanded views of key groups identified in FIG. 5.
Figure 5B:
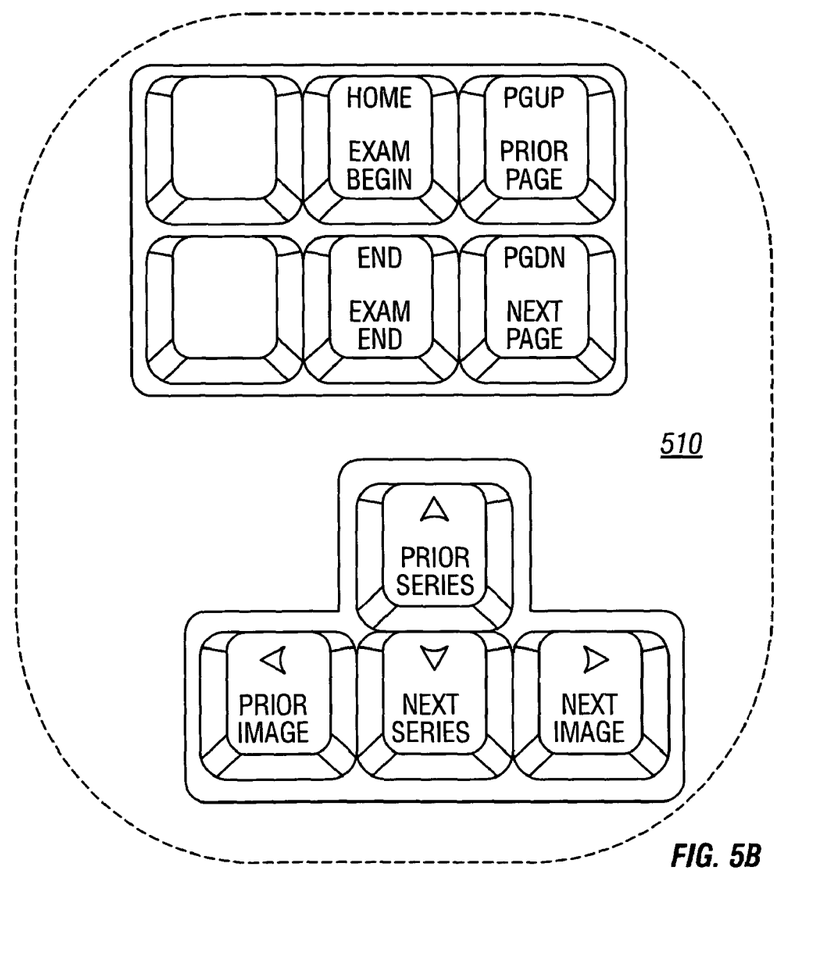
Figure 5C:
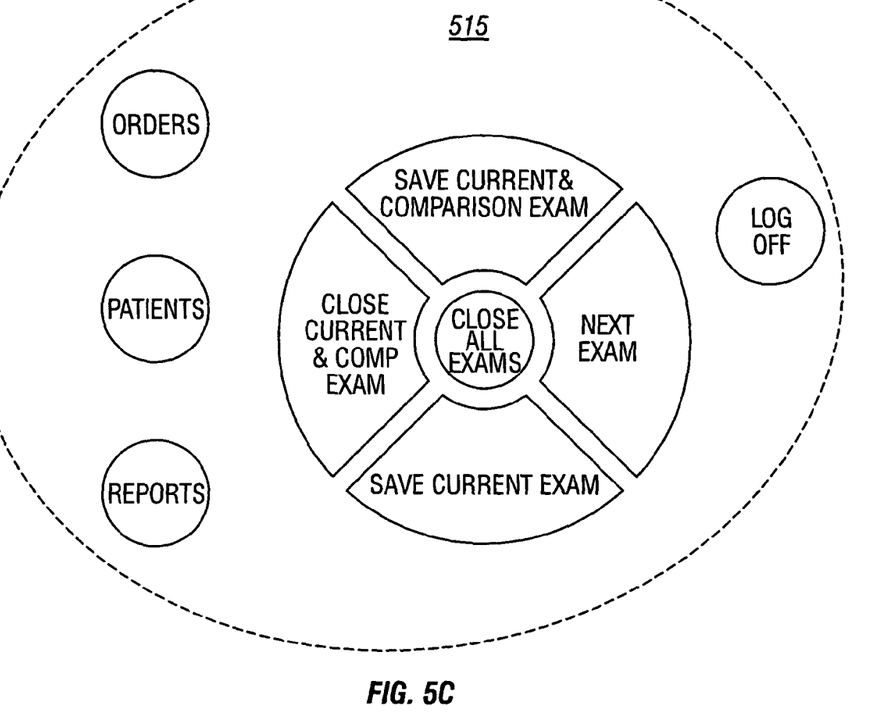
Figure 5D:
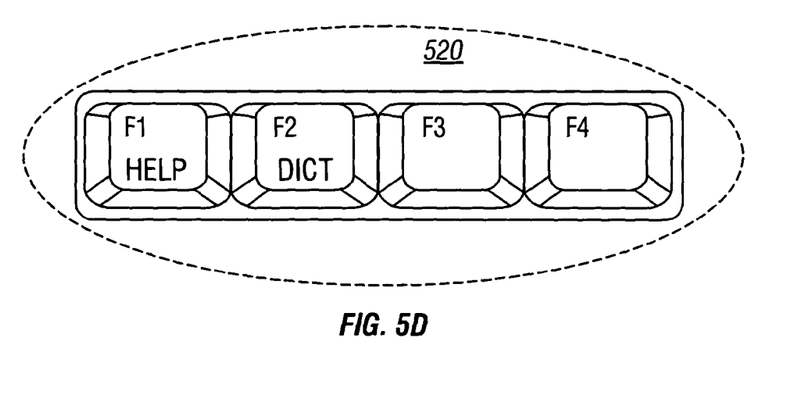

FIG. 5 shows keyboard 500 in accordance with one embodiment of the invention that is adapted to function with the Centricity™ PACS Workstation Software from GE Medical System. In this particular embodiment, color-coded key groups are provided for image display functions (see key group 505 in FIG. 5A), image navigation functions such as image selection and window and level adjustment functions (see key group 510 in FIG. 5B), patient information functions (se key group 515 in FIG. 5C) and user support functions such as program help and physician dictation functions (see key group 520 in FIG. 5D). While key groups 505–520 in FIGS. 5A–5D are shown as having only icons or only text to denote their function, any key or key group could use both iconic and textual labels.

Figure 6:
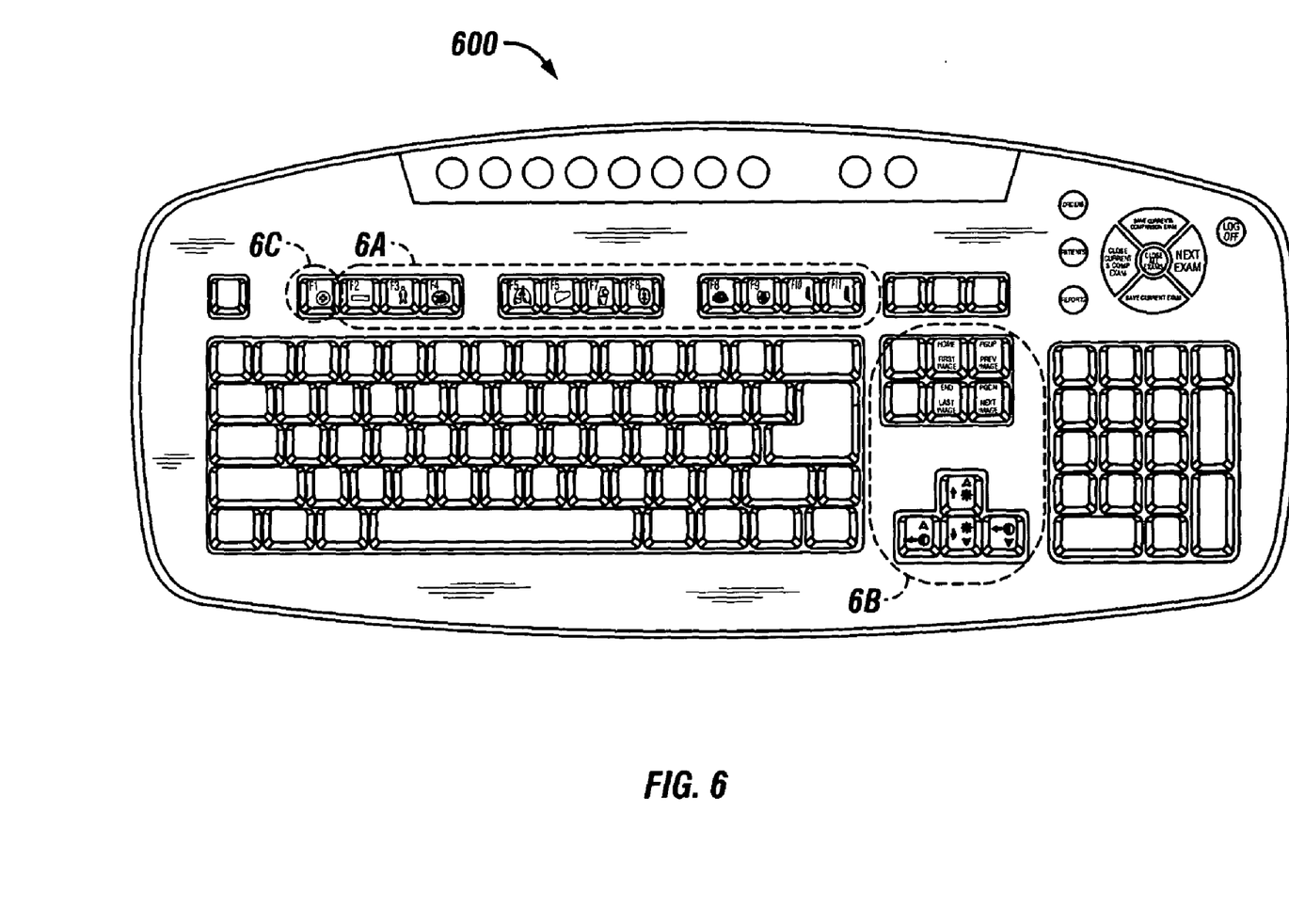
FIG. 6 shows a keyboard in accordance with another embodiment of the invention.
Figure 6A:
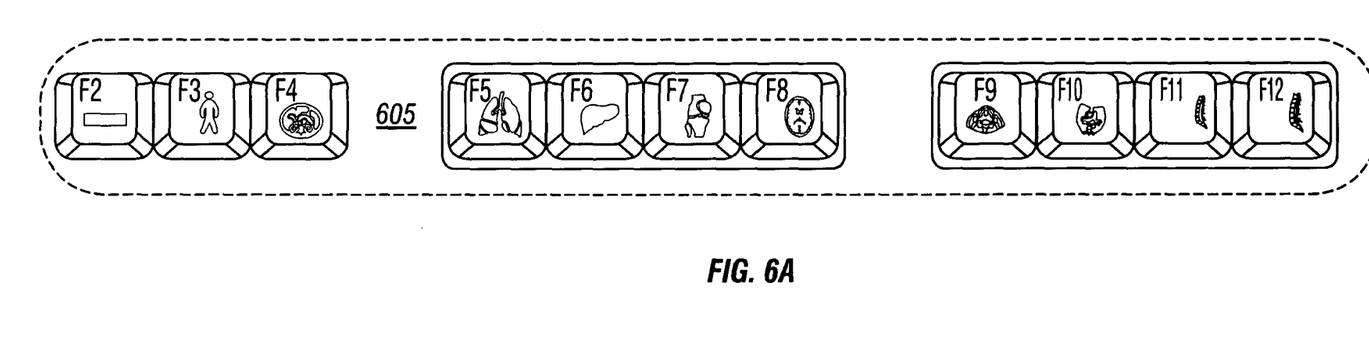
FIGS. 6A through 6C show expanded views of key groups identified in FIG. 6.
Figure 6B:
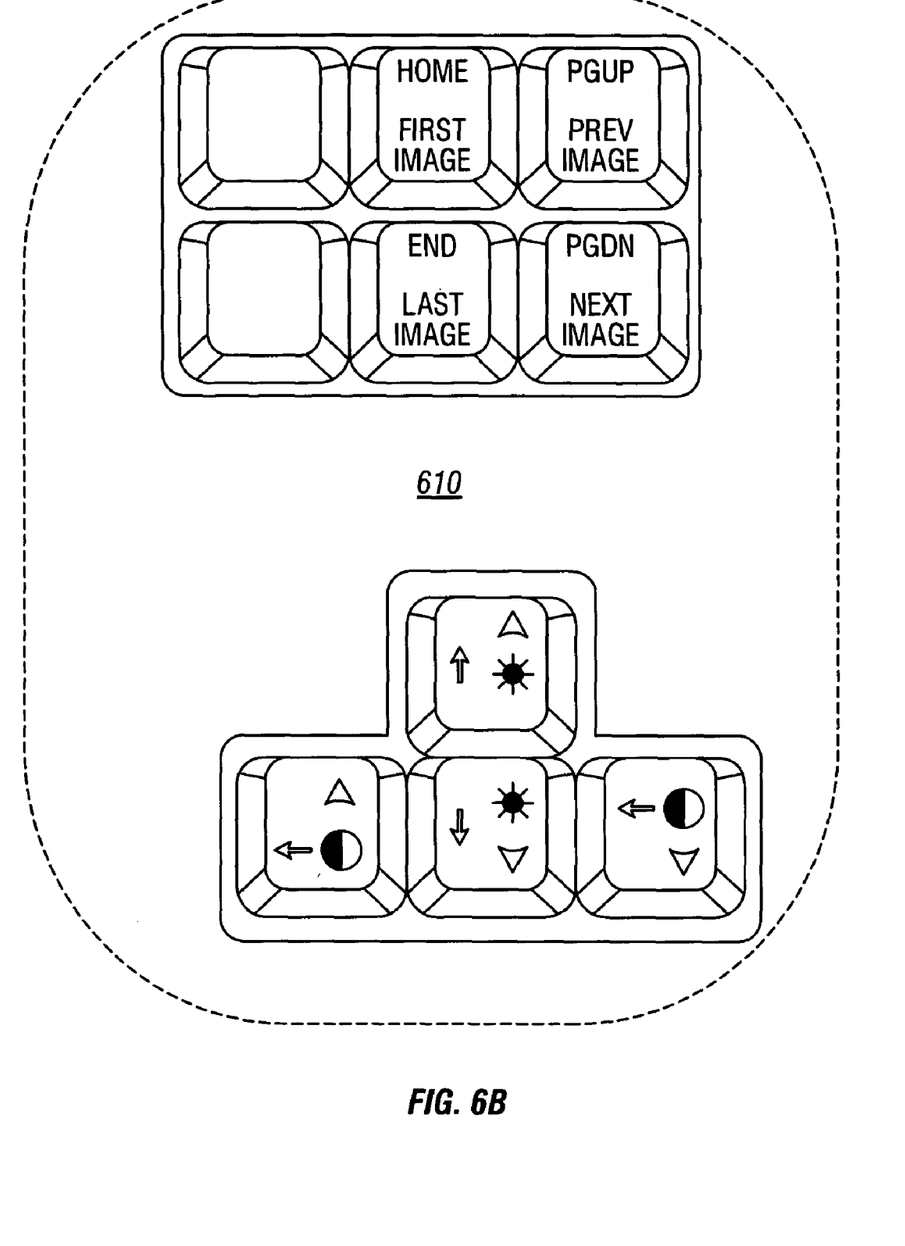
Figure 6C:
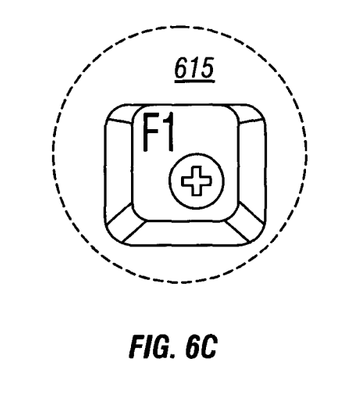

FIG. 6 shows keyboard 600 in accordance with another embodiment of the invention that is adapted to function with the eFilm workstation software application from Merge eFilm of Milwaukee, Wis. In this embodiment, color-coded key groups are provided for image display functions (see key group 605 in FIG. 6A), image navigation functions such as image selection and window and level adjustment functions (see key group 610 in FIG. 6B) and user support functions such as program help (see key group 615 in FIG. 6C). While key groups 605–615 in FIGS. 6A–6C are shown as having only icons or only text to denote their function, any key or key group could use both iconic and textual labels.

Figure 7:
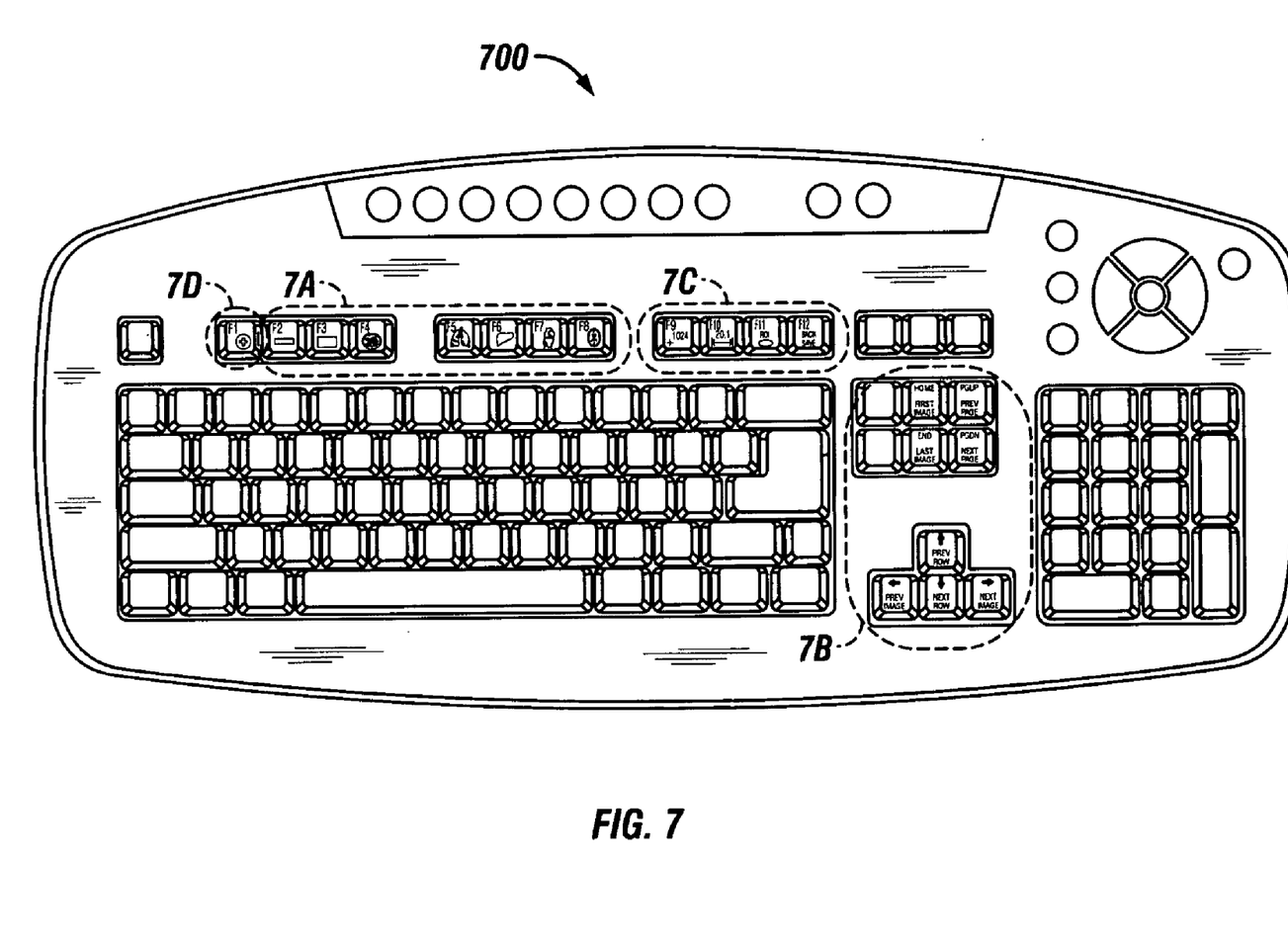
FIG. 7 shows a keyboard in accordance with yet another embodiment of the invention.
Figure 7A:
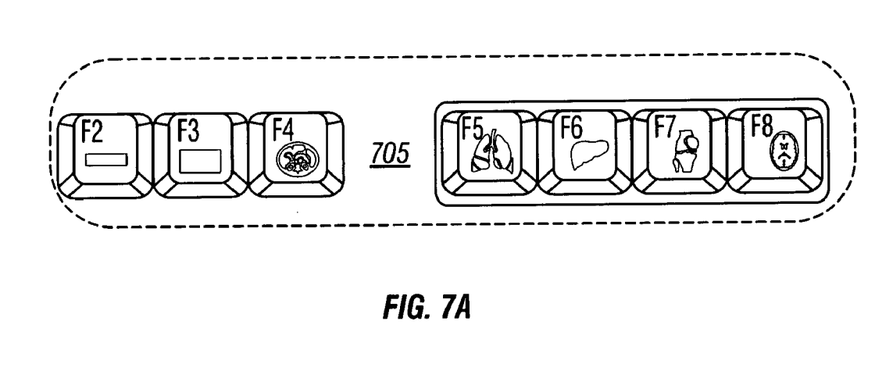
FIGS. 7A through 7D show expanded views of key groups identified in FIG. 7.
Figure 7B:
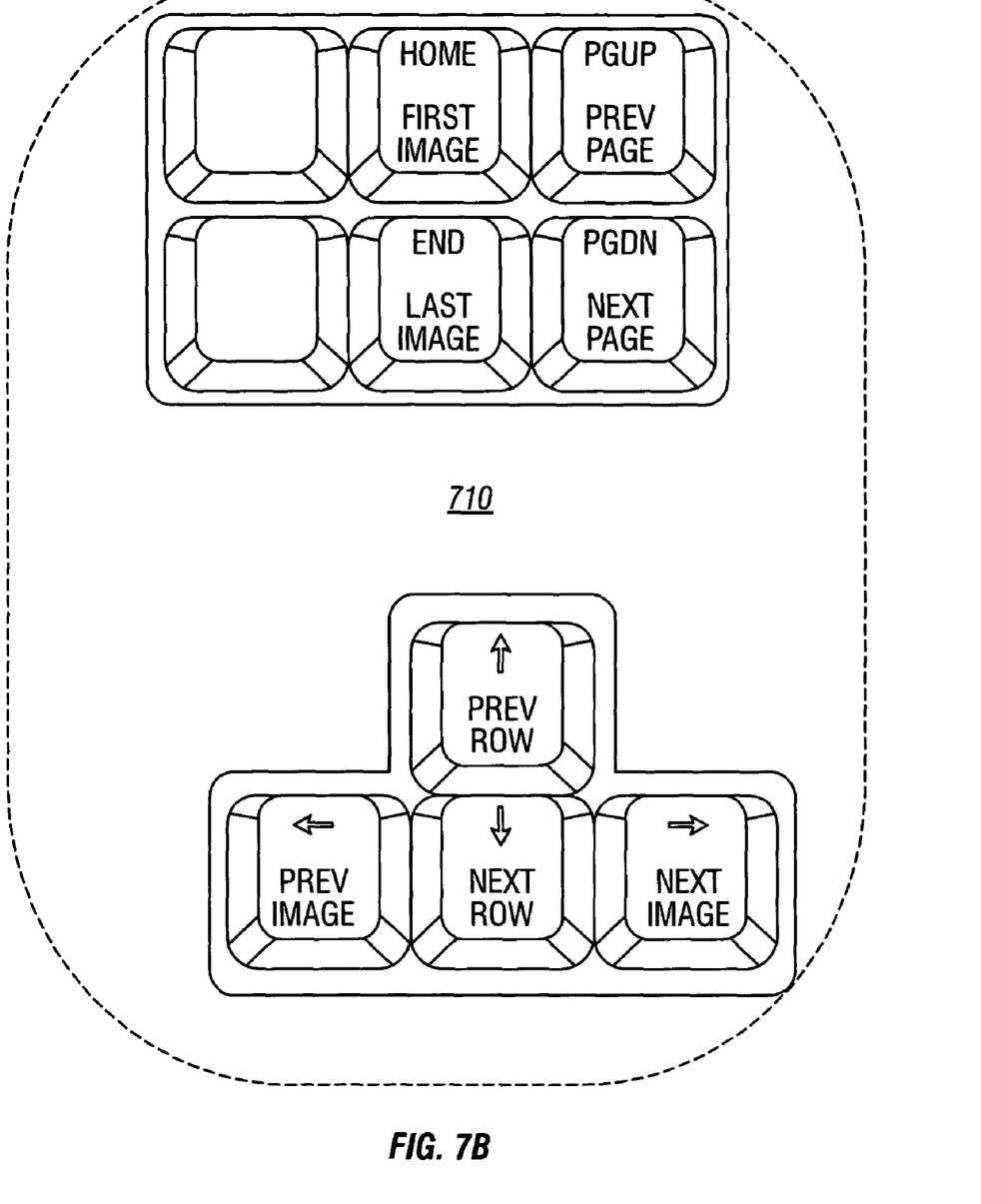
Figure 7C:
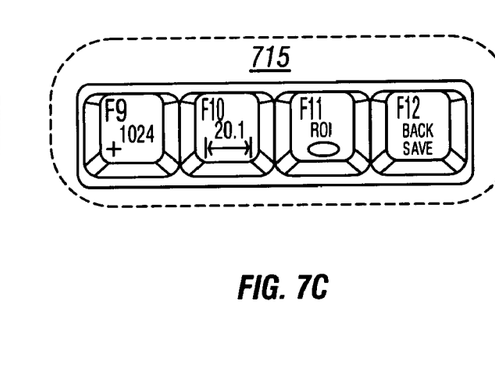
Figure 7D:
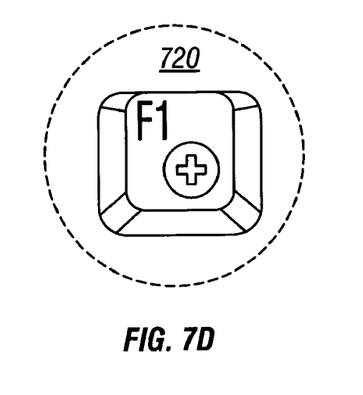

FIG. 7 shows yet another keyboard in accordance with the invention adapted to function with the RadWorks software from GE Medical Systems. In this embodiment, color-coded key groups are provided for image display functions (see key group 705 in FIG. 7A), image navigation functions (see key group 710 in FIG. 7B), image measurement functions such as display Hounsfeld units (F9), measure distance (F10), display details on designated Region of Interest (F11) and return to patient list saving changes (F12) (see key group 715 in FIG. 7C) and user support functions such as program help (see key group 720 in FIG. 7D). While key groups 705–720 in FIGS. 7A–7D are shown as having only icons or only text to denote their function, any key or key group could use both iconic and textual labels.

As shown in FIGS. 5 through 7, keys within a key group are typically adjacent. That is, keys in the first key group (e.g., the image display key group) are located in one area of the keyboard while keys in a second key group (e.g., the image manipulation key group) are located in another area of the keyboard. While this is not necessary, it has been found that this arrangement makes it easier and faster for users (new and experienced) to select the desired function.

Various changes in the details of the preferred embodiments described above are possible. For instance, the number, color, shape, location and geometric grouping of key groups (e.g., image display, image navigation, image manipulation, and patient information function groups) of keys as well as the specific icons associated therewith may be changed without falling outside the below claims. In addition, key groups other than those described above could be defined. For example, if a medical software application permits the user to control and acquire images from an imaging device, key functions associated with these operations may be assigned to keys comprising a key group. Further, keys having assigned icons may also include text descriptions (see FIG. 3) or, in the alternative, icons may be entirely replaced with text descriptions (see FIG. 4). Further, a single key group as described herein, could be divided into two or more key groups with each such sub-group having a different visually distinct characteristic (e.g., color).

While the invention has been disclosed with respect to a limited number of embodiments, numerous modifications and variations will be appreciated by those skilled in the art. It is intended, therefore, that the following claims cover all such modifications and variations that may fall within the true sprit and scope of the invention.

What is claimed is:

1. A keyboard for use with a medical software application program, comprising:
   a first plurality of keys having a first visually distinguishing characteristic, wherein keys in the first plurality of keys include an icon representative of an image display function such that when a key from the first plurality of keys is activated, the image display function represented by the icon associated with the activated key is performed by the medical software application program; and
   a second plurality of keys having a second visually distinguishing characteristic, wherein the second plurality of keys include an indication representing an image navigation function such that when a key from the second plurality of keys is activated, the image navigation function associated with the activated key is performed by the medical software application program.

2. The keyboard of claim 1, further comprising a third plurality of keys having a third visually distinguishing characteristic, wherein the third plurality of keys includes an indication representative of an image manipulation function such that when a key from the third plurality of keys is activated, the image manipulation function represented by the indication associated with the activated key is performed by the medical software application program.

3. The keyboard of claim 2, further comprising a fourth plurality of keys having a fourth visually distinguishing characteristic, wherein the fourth plurality of keys includes an indication representative of a patient information function such that when a key from the fourth plurality of keys is activated, the patient information function represented by the indication associated with the activated key is performed by the medical software application program.

4. The keyboard of claim 1, wherein the first visually distinguishing characteristic comprises a first color.

5. The keyboard of claim 4, wherein the second visually distinguishing characteristic comprises a second color, wherein the second color is different from the first color.

6. The keyboard of claim 2, wherein the first visually distinguishing characteristic comprises a first color, the second visually distinguishing characteristic comprises a second color different from the first color, and the third visually distinguishing characteristic comprises a third color different from the first and second colors.

7. The keyboard of claim 3, wherein the first visually distinguishing characteristic comprises a first color, the second visually distinguishing characteristic comprises a second color different from the first color, the third visually distinguishing characteristic comprises a third color different from the first and second colors, and the fourth visually distinguishing characteristic comprises a fourth color different from the first, second and third colors.

8. The keyboard of claim 1, wherein each key in the first plurality of keys includes an icon representing a radiological display function.

9. The keyboard of claim 8, wherein the radiological display functions are associated with predetermined body regions.

10. The keyboard of claim 9, wherein the predetermined body regions are selected from the group consisting of one or more of the head, neck, lung, liver, knee, abdomen, bone, spine, mediastium, pelvis and whole body.

11. The keyboard of claim 8, wherein the radiological display functions include window and level presets for display of a radiographic image.

12. The keyboard of claim 1, wherein the first plurality of keys further comprise a text label indicative of the display function associated with the key.

13. The keyboard of claim 1, wherein each of the first plurality of keys is adjacent to at least one other of the first plurality of keys.

14. The keyboard of claim 1, wherein the image navigation functions are selected from the group consisting of one or more of first image, last image, next image, previous image, next series, previous series, first series and last series.

15. The keyboard of claim 1, wherein at least one of the indications for the second plurality of keys comprise a text label.

16. The keyboard of claim 15, wherein at least one of the indications for the second plurality of keys further comprise an icon.

17. The keyboard of claim 1, wherein each of the second plurality of keys is adjacent to at least one other of the second plurality of keys.

18. The keyboard of claim 2, wherein the image manipulation functions are selected from the group consisting of one or more of retrieve patient information, measurement tools, synchronization of images, image filters and presets, cross correlation, 3D reconstruction.

19. The keyboard of claim 18, wherein at least one of the indications for the third plurality of keys comprise an icon.

20. The keyboard of claim 19, wherein at least one of the indications for the third plurality of keys further comprise a text label.

21. The keyboard of claim 2, wherein each of the third plurality of keys is adjacent to at least one other of the third plurality of keys.

22. The keyboard of claim 3, wherein each of the third plurality of keys is adjacent to at least one other of the third plurality of keys.

23. The keyboard of claim 1, wherein the medical software application program comprises a radiographic software application program.

* * * * *